United States Patent
Ikurumi et al.

(10) Patent No.: US 7,199,816 B2
(45) Date of Patent: Apr. 3, 2007

(54) DEVICE AND METHOD FOR PICKING UP IMAGE OF COMPONENT, AND COMPONENT MOUNTING APPARATUS

(75) Inventors: Kazuhiro Ikurumi, Katano (JP); Yutaka Mitsumoto, Okayama (JP); Eiichi Hachiya, Kofu (JP); Hideshi Ueda, Yao (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 639 days.

(21) Appl. No.: 10/720,089

(22) Filed: Nov. 25, 2003

(65) Prior Publication Data

US 2004/0150742 A1    Aug. 5, 2004

(30) Foreign Application Priority Data

Nov. 29, 2002    (JP)    ............................. 2002-347321

(51) Int. Cl.
*H04N 7/18*    (2006.01)

(52) U.S. Cl. .......................... 348/87; 348/86; 348/125; 348/126

(58) Field of Classification Search .......... 348/80–130; 356/372–394; 382/145, 318
See application file for complete search history.

(56) References Cited

U.S. PATENT DOCUMENTS

| 4,253,112 | A | * | 2/1981 | Doemens | ...................... | 348/87 |
| 4,466,073 | A | * | 8/1984 | Boyan et al. | ................ | 356/400 |
| 4,899,921 | A | * | 2/1990 | Bendat et al. | .............. | 228/105 |
| 5,528,371 | A | * | 6/1996 | Sato et al. | ................... | 356/625 |
| 5,699,447 | A | * | 12/1997 | Alumot et al. | .............. | 382/145 |
| 6,986,196 | B2 | * | 1/2006 | Terui | ........................... | 29/740 |

FOREIGN PATENT DOCUMENTS

| JP | 60-1900 | 1/1985 |
| JP | 2003-174292 | 6/2003 |

* cited by examiner

*Primary Examiner*—Andy Rao
(74) *Attorney, Agent, or Firm*—Wenderoth, Lind & Ponack, L.L.P.

(57) ABSTRACT

An image pickup camera is arranged, so that a plurality of components are adapted to be sequentially imaged by corresponding image pickup device with a timing whereby light for imaging is prevented from affecting the other image pickup operation while the components are let to pass above the image pickup camera. The hold posture of each of the plurality of components can be imaged separately without decreasing the cycle time.

14 Claims, 8 Drawing Sheets

Fig.5

| PARAMETER | | SEQUENCE | 0 | 1 | 2 | | 8 | 9 |
|---|---|---|---|---|---|---|---|---|
| IMAGE PICKUP DEVICE SMALL/LARGE | | VISUAL FIELD PATTERN | 00 | 01 | 02 | | 08 | 09 |
| | | LED UPPER STAGE | 10 | 11 | 12 | | 18 | 19 |
| | | LED MIDDLE STAGE | 20 | 21 | 22 | | 28 | 29 |
| | | LED LOWER STAGE | 30 | 31 | 32 | | 38 | 39 |
| IMAGE PICKUP DEVICE SMALL/LARGE | | VISUAL FIELD PATTERN | 50 | 51 | 52 | | 58 | 59 |
| | | LED UPPER STAGE | 60 | 61 | 62 | | 68 | 69 |
| | | LED MIDDLE STAGE | 70 | 71 | 72 | 77 | 78 | 79 |
| | | LED LOWER STAGE | 80 | 81 | 82 | 87 | 88 | 89 |
| IMAGE PICKUP DEVICE SMALL/LARGE | | VISUAL FIELD PATTERN | A0 | A1 | | A7 | A8 | A9 |
| | | LED UPPER STAGE | B0 | B1 | | B7 | B8 | B9 |
| | | LED MIDDLE STAGE | C0 | C1 | | C7 | C8 | C9 |
| | | LED LOWER STAGE | E0 | E1 | | E7 | E8 | E9 |

160

DEVICE AND METHOD FOR PICKING UP IMAGE OF COMPONENT, AND COMPONENT MOUNTING APPARATUS

BACKGROUND OF THE INVENTION

The present invention relates to, for example, an image pickup method for electronic components to be mounted on a printed circuit board, a component image pickup apparatus that carries out the image pickup method, and a component mounting apparatus with the component image pickup apparatus.

Improving reliability on a working process and shortening a cycle time are greatly required in order to improve productivity in a mounting process for electronic components in these years. Conventionally, in a mounting apparatus for mounting electronic components such as chip components and IC components onto a circuit board, a suction posture of the electronic component at a nozzle that holds the electronic component and mounts the same to the circuit board is picked up with the use of an image pickup device such as a CCD camera. A suction state, a suction position and the like are recognized on the basis of the picked up-image, and positions of the nozzle and a head having the nozzle are corrected in accordance with recognized information so that the electronic component can be correctly mounted at a mounting position on the circuit board. Components are mounted in this manner (see, for instance, publication of unexamined Japanese patent application No. 60-1900).

For further improving the productivity recently, an idea is conceived that a plurality of nozzles for sucking electronic components are arranged, thereby transferring a plurality of electronic components to a mounting area at a time to mount the same. In picking up images of the components as above in this configuration, while it is necessary to pick up image of the suction state of each of electronic components sucked by the plurality of nozzles, each of the electronic components should be picked up through illumination under an illumination condition conforming to the each electronic component because the electronic components sucked by the nozzles are different in types.

As a method for picking up an image, it is possible to pick up image of the electronic components one by one with the use of one camera and one illumination device, which unfavorably takes a long time. For example, given that 5 nozzles are arranged in an array by a pitch of 10.75 mm to require 10 ms to move by each pitch, and 33 ms is necessary to transfer the obtained image, a total of 205 ms is necessitated.

On the other hand, if image pickup is to be carried out at a time by using a plurality of cameras and preparing a plurality of illumination devices, in the case, e.g., where a nozzle interval is short as in an arrangement by the pitch of 10.75 mm, light from each illumination devices interfere with each other, thereby obstructing normal imaging.

The present invention is developed to solve the problem, and has for its object to provide a component image pickup apparatus for picking up images of hold postures of a plurality of components separately without decreasing a cycle time, a component image pickup method carried out by the component image pickup apparatus, and a component mounting apparatus with the component image pickup apparatus.

SUMMARY OF THE INVENTION

In order to accomplish the above objective, the present invention is configured as described below.

Specifically, according to a first aspect of the present invention, there is provided a component image pickup apparatus including:

a component holding head which has a plurality of component holding members and for moving in a movement direction; and an image pickup camera for picking up an image of each of components held by the component holding members, the image pickup camera comprising:

a plurality of image pickup devices arranged corresponding to a plurality of paths respectively where the component holding members pass by the movement in the movement direction, for picking up the images of the components held by the component holding members;

single illuminator arranged for the plurality of image pickup devices for applying light at an image pickup operation by each image pickup device; and an image pickup controller for controlling the image pickup operation to each image pickup device and the illuminator in accordance with an image pickup condition related to each image pickup device and set for every component and an illumination condition related to the illuminator.

The component image pickup apparatus of the first aspect may be designed so that the device further comprises a recognizer connected to the image pickup camera for supplying the image pickup condition and the illumination condition to the image pickup controller before the component holding head reaches above the image pickup camera, controlling the image pickup operation to each image pickup device and the illuminator, and receiving image information from each image pickup device after the imaging.

The component image pickup apparatus of the first aspect may be designed so that the image pickup devices are disposed at respective setting positions where the image pickup devices pick up the images of components one by one with a time difference in accordance with the movement of the component holding members in the movement direction.

The component image pickup apparatus of the first aspect may be designed so that the setting positions of a first image pickup device and a second image pickup device for imaging next to the first image pickup device are disposed at positions separated by at least a distance which is obtained by multiplying a moving velocity in the movement direction of the component holding head and an exposure time at the first image pickup device.

The component image pickup apparatus of the first aspect may be designed so that the component holding members are arranged at equal intervals along a circumference, while the movement direction is a direction parallel to a diametrical direction of the circumference and passing through two of the component holding members arranged at the equal intervals.

Further, according to a second aspect of the present invention, there is provided a component image pickup method comprising:

supplying an image pickup condition and an illumination condition necessary for imaging each of components and set for every component to an image pickup camera while a component holding head with a plurality of component holding members moves to above the image pickup camera which has a plurality of image pickup devices for imaging respective components held by the component holding members, and single illuminator;

letting the component holding head pass above the image pickup camera along a movement direction without stopping the head after the supplying; and sequentially imaging the components by the respective image pickup devices during the passing with a timing whereby effects of light for imaging of the illuminator are avoided.

Further, according to a third aspect of the present invention, there is provided a component mounting apparatus comprising:

a component image pickup apparatus;

a component holding head having a plurality of component holding members respectively for holding electronic components and mounting the held electronic components to a circuit board;

a drive unit for moving the component holding head in a movement direction; and a circuit board holding unit for holding the circuit board, the component image pickup apparatus including:

an image pickup camera for picking up an image of each of components held by the component holding members, the image pickup camera having:

a plurality of image pickup devices arranged corresponding to a plurality of paths respectively where the component holding members pass by the movement in the movement direction, for picking up the images of the components held by the component holding members;

single illuminator arranged for the plurality of image pickup devices for applying light at an image pickup operation by each image pickup device; and an image pickup controller for controlling the image pickup operation to each image pickup device and the illuminator in accordance with an image pickup condition related to each image pickup device and set for every component and an illumination condition related to the illuminator.

According to the component image pickup apparatus of the first aspect, the component image pickup method of the second aspect and the component mounting apparatus of the third aspect of the present invention, there is included the image pickup camera, and a plurality of components are adapted to be sequentially imaged by respective image pickup devices at the timing whereby the light for imaging is prevented from affecting the other image pickup operation while the plurality of components are let to pass above the image pickup camera. The hold posture of the plurality of components can be imaged separately without decreasing the cycle time.

Moreover, since the image pickup condition and the illumination condition necessary for the image pickup operation for all of the components are preliminarily supplied to the image pickup camera before imaging is started, the need of transferring the image pickup condition and the illumination condition at every time of imaging each component is eliminated and the communication delay is prevented. The components to be imaged can be moved at a higher speed and can be imaged as well.

The image pickup camera can be equipped with the recognizer, and according to this arrangement, an operation load of the image pickup camera can be reduced.

BRIEF DESCRIPTION OF THE DRAWINGS

These and other aspects and features of the present invention will become clear from the following description taken in conjunction with the preferred embodiments thereof with reference to the accompanying drawings, in which:

FIG. 5 is a diagram of an example of parameter data necessary for the image pickup operation carried out by the component image pickup apparatus of FIG. 1;

DETAILED DESCRIPTION OF THE PREFERRED EMBODIMENTS

Figure 1:
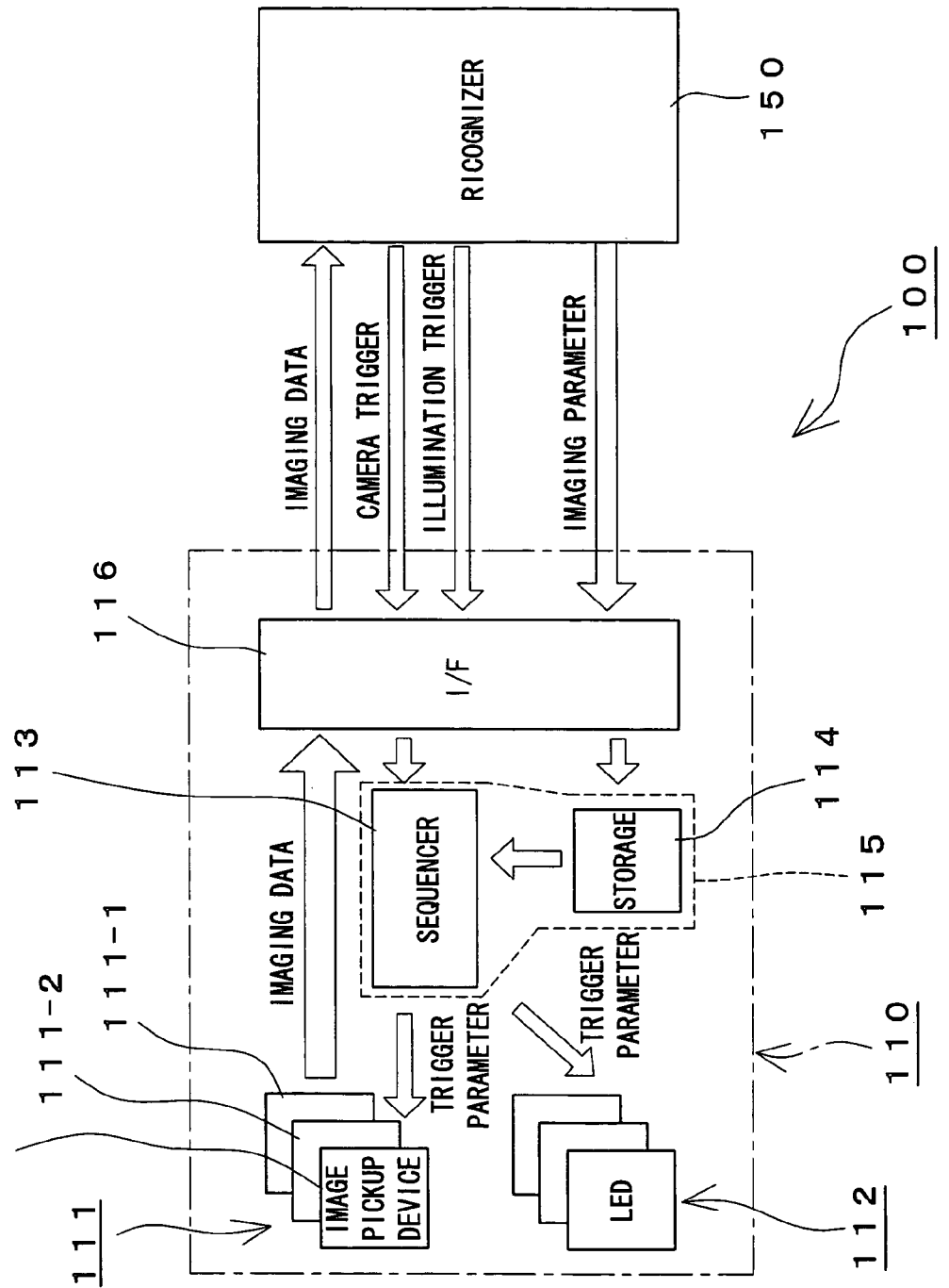
FIG. 1 is a block diagram showing the configuration of a component image pickup apparatus according to an embodiment of the present invention.

A component image pickup apparatus, a component image pickup method and a component mounting apparatus as embodiments of the present invention will be described hereinafter with reference to drawings. The component image pickup method is a method carried out by the component image pickup apparatus, and the component mounting apparatus includes the component image pickup apparatus. Like parts are designated by like reference numerals throughout the drawings.

Figure 2:
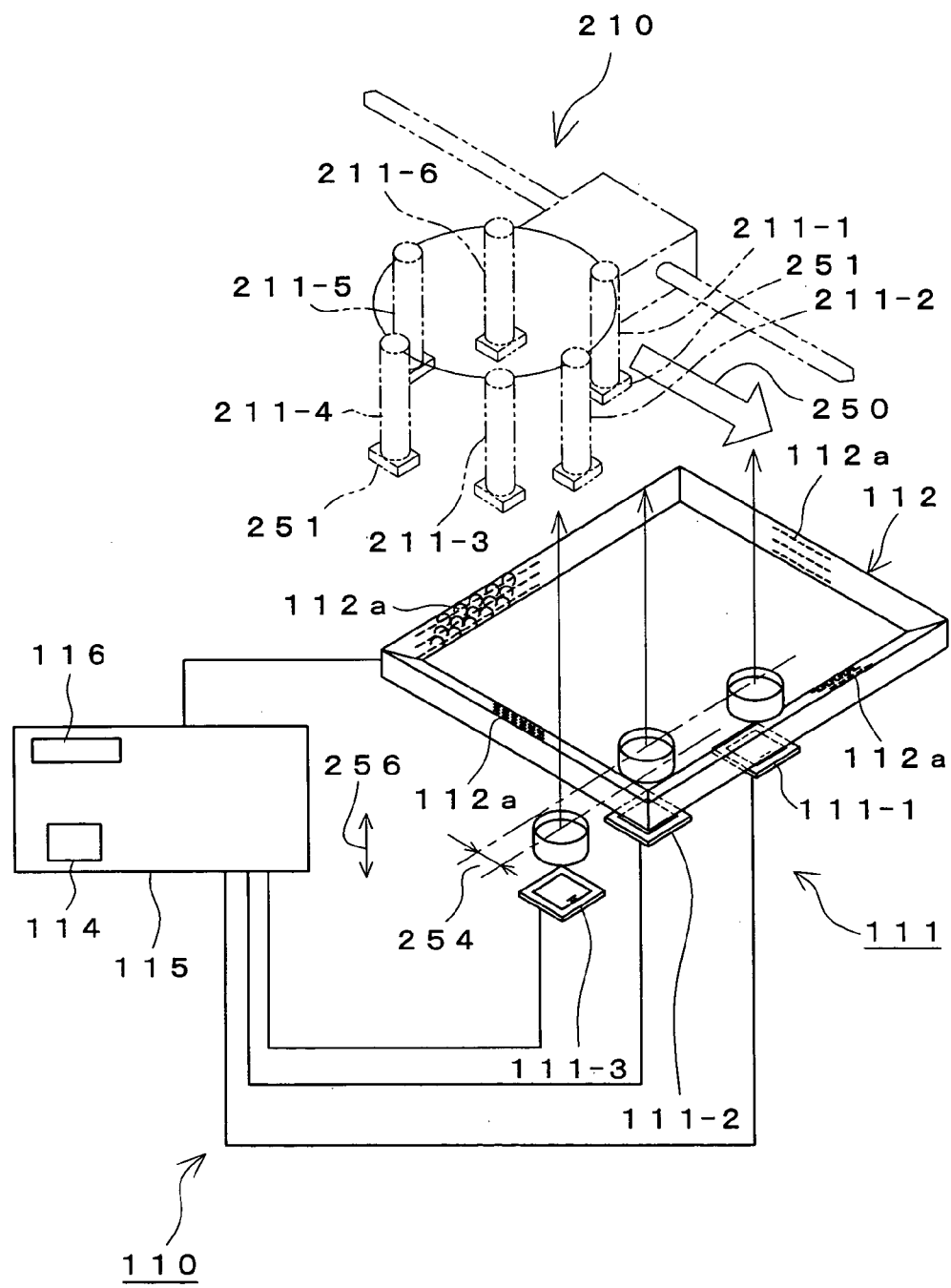
FIG. 2 is a perspective view showing the configuration of an image pickup camera part in FIG. 1.

As indicated in FIGS. 1 and 2, the component image pickup apparatus has an image pickup camera 110 which is equipped with a plurality of image pickup devices 111, single illuminator 112, and an image pickup controller 115 with a sequencer 113 and a storage 114, as fundamental constituent parts. The component image pickup apparatus can include a recognizer 150 to be connected to the image pickup camera 110. The image pickup camera 110 has an interface 116 formed as a connecting part to the recognizer 150.

This component image pickup apparatus 100 is a device for picking up each of images of components 251 held by each suction nozzle 211 when a component holding head 210 moves in a movement direction 250, as shown in FIG. 2. The component holding head 210 has six suction nozzles 211, namely, suction nozzles 211-1 to 211-6 as an example functioning as a component holding member, which are arranged at equal intervals by every 60° of a central angle on a circumference.

Figure 3:
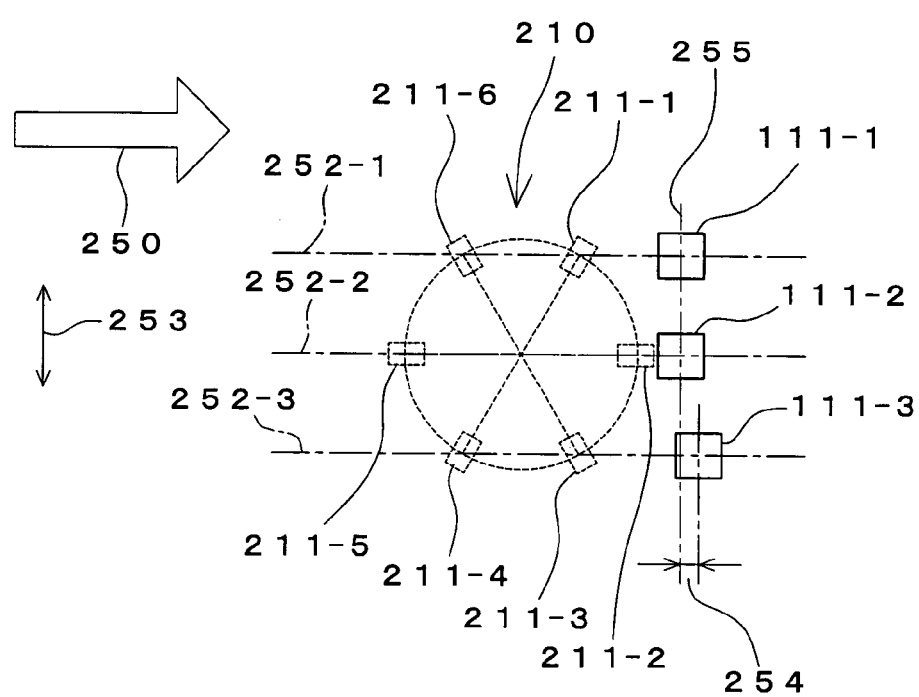
FIG. 3 is a diagram explanatory of an order of image pickup carried out by the component image pickup apparatus of FIG. 1.

According to the present embodiment as above, the component holding head 210 has the six suction nozzles 211 arranged at equal intervals on the circumference. Therefore, three paths 252-1 to 252-3 (generically denoted as the path 252 in some cases) each passing two suction nozzles 211 can be formed in a diametrical direction of the circumference and in a direction parallel to the movement direction 250 as shown in FIG. 3. For example, suction nozzles 211-1 and 211-6 pass the path 252-1, suction nozzles 211-2 and 211-5 pass the path 252-2, and suction nozzles 211-3 and 211-4 pass the path 252-3. The image pickup device 111 are disposed correspondingly to the paths 252-1 to 252-3 respectively. More specifically, image pickup device 111-1, 111-2 and 111-3 are disposed below the path 252-1, below the path 252-2 and below the path 252-3 respectively. Moreover, the image pickup device 111-1 and 111-2 are arranged on the same axis 255 along an orthogonal direction 253 orthogonal to the movement direction 250. The image pickup device 111-1 and 111-2 are arranged by a shift or displacement of a distance 254 in the movement direction 250 from the image pickup device 111-3.

The reason that the image pickup device 111-1 and the image pickup device 111-2 can be arranged on the same axis 255 is that, as is clear from FIG. 3, the suction nozzles 211-1 and 211-2 are disposed at displaced positions in the movement direction 250 because of the arrangement in the embodiment in which the suction nozzles 211 are arranged at six points respectively via the equal interval on the circumference, thereby allowing the image pickup device 111-1 and 111-2 to pick up images at different timings. In contrast to this, the suction nozzle 211-1 and the suction nozzle 211-3 are disposed at the same position in the movement direction 250, and therefore the image pickup device 111-3 is displaced by the distance 254 to the image pickup device 111-1 and 111-2 based on the reason to be described below.

The reason for the above arrangement with the displacement is that the image pickup device 111-1 to 111-3 need to pick up images one by one so that light for picking up the image from one of the image pickup devices 111 in an image pickup operation does not affect other image pickup operations of remaining pickup devices 111.

In the case, e.g., where the image pickup device 111-1 carries out the image pickup operation and the image pickup device 111-3 is to carry out the image pickup operation next, the above-referred distance 254 between the image pickup device 111-1 and the image pickup device 111-3 can be a value obtained by multiplying a moving velocity in the movement direction 250 of the component holding head 210 and an exposure time at the image pickup device 111-1. By arranging with the displacement of at least the above distance 254, two image pickup devices 111 which are to carry out the image pickup operation continuously, each of the exposure at the two image pickup devices 111 is prevented from overlapping.

Figure 4:
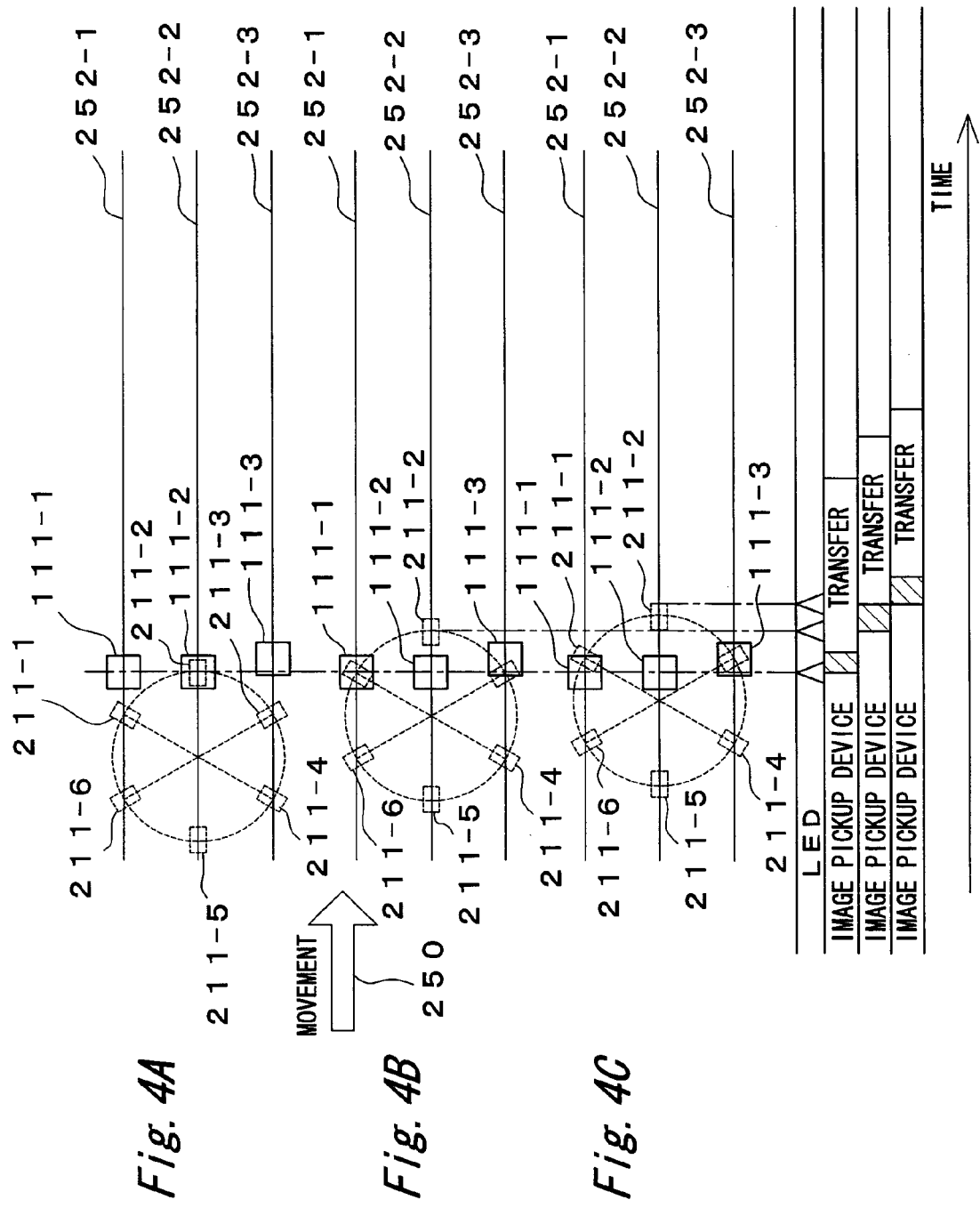
FIGS. 4A, 4B, and 4C are diagrams explanatory of a timing of an image pickup operation carried out by the component image pickup apparatus of FIG. 1.

When the suction nozzles 211 and the image pickup devices 111 are arranged as described hereinabove, the image pickup devices 111-1 to 111-3 can pick up the images of the components 251 at mutually different timings without overlapping the exposure respectively. In other words, as shown in FIG. 4, in accordance with the move of the component holding head 210 in the movement direction 250 without stopping, the image of the component 251 held by the suction nozzle 211-2 is first picked up by the image pickup device 111-2 as indicated by FIG. 4A, the image of the component 251 held by the suction nozzle 211-1 is picked up next by the image pickup device 111-1 as indicated by FIG. 4B, and then the image of the component 251 held by the suction nozzle 211-3 is picked up by the image pickup device 111-3 as indicated by FIG. 4C.

Although the image pickup devices 111 are arranged correspondingly to the paths 252 where the plurality of nozzles 211 can pass in common as described here in the embodiment from a viewpoint of reducing the number of image pickup devices 111 as much as possible, if it is not necessary to take reducing the number of image pickup devices, or the like into account, each image pickup device 111 can be arranged correspondingly to the path for each suction nozzle 211 along the movement direction 250.

Also from the viewpoint of reducing the number of image pickup devices, six suction nozzles 211 are aligned on the circumference as illustrated in the embodiment. However, the present invention is not limited to the embodiment. The number of suction nozzles 211 is not limited. Moreover, an arrangement direction of the suction nozzles 211 is not limited to on the circumference and the suction nozzles can be, for instance, arranged in an array along an arrangement direction of holding members.

Single illuminator 112 is installed for the image pickup devices 111-1 to 111-3 as indicated in FIG. 2, which is a device for providing illumination for picking up the image at the image pickup operation of each image pickup device 111. In the present embodiment, the illuminator 112 has LEDs 112a as a light source fitted in three, namely, upper, middle and lower stages along an up-down direction 256 orthogonal to the movement direction 250 and to the orthogonal direction 253.

The image pickup controller 115 is a device for making each image pickup device 111 and the illuminator 112 carry out the image pickup operation according to an image pickup condition for each image pickup device 111 set for every component 251 to be imaged, and an illumination condition for the illuminator 112.

The storage 114 included in the image pickup controller 115 is a part for storing a parameter data 160 as represented in FIG. 5 that is sent from the recognizer 150. The parameter data 160 corresponds to the above image pickup condition and illumination condition in the embodiment. These image pickup condition and illumination condition are set correspondingly to each sequence of picking up each of components 251. The image pickup condition is information for designating a large visual field imaging or a small visual field imaging to the image pickup devices 111, while the illumination condition is a condition for designating a luminance to the illuminator 112. Since the illuminator 112 has LEDs 112a arranged in three stages as described above according to the embodiment, the illumination condition is information for indicating which of the three stages of the LEDs 112a is (are) to emit light. At least one of the three stages is adapted to emit light.

The sequencer 113 included in the image pickup controller 115 reads out the parameter data 160 from the storage 114 and sends the image pickup condition and the illumination condition for each sequence to the image pickup devices 111 and the illuminator 112. Operations of the image pickup controller 115 will be detailed by the following description of the image pickup operation.

The recognizer 150 sends the parameter data 160 to the image pickup camera 110 as above, and moreover generates a trigger signal for starting picking up image by the image pickup device 111 and the illuminator 112 and sends the trigger signal to the image pickup device 111 and the illuminator 112. Furthermore, after picking up image, the recognizer 150 receives a picked up image information from the image pickup camera 110 and carries out image processing to analyze a hold posture of the component 251 held by the suction nozzle 211.

Figure 8:
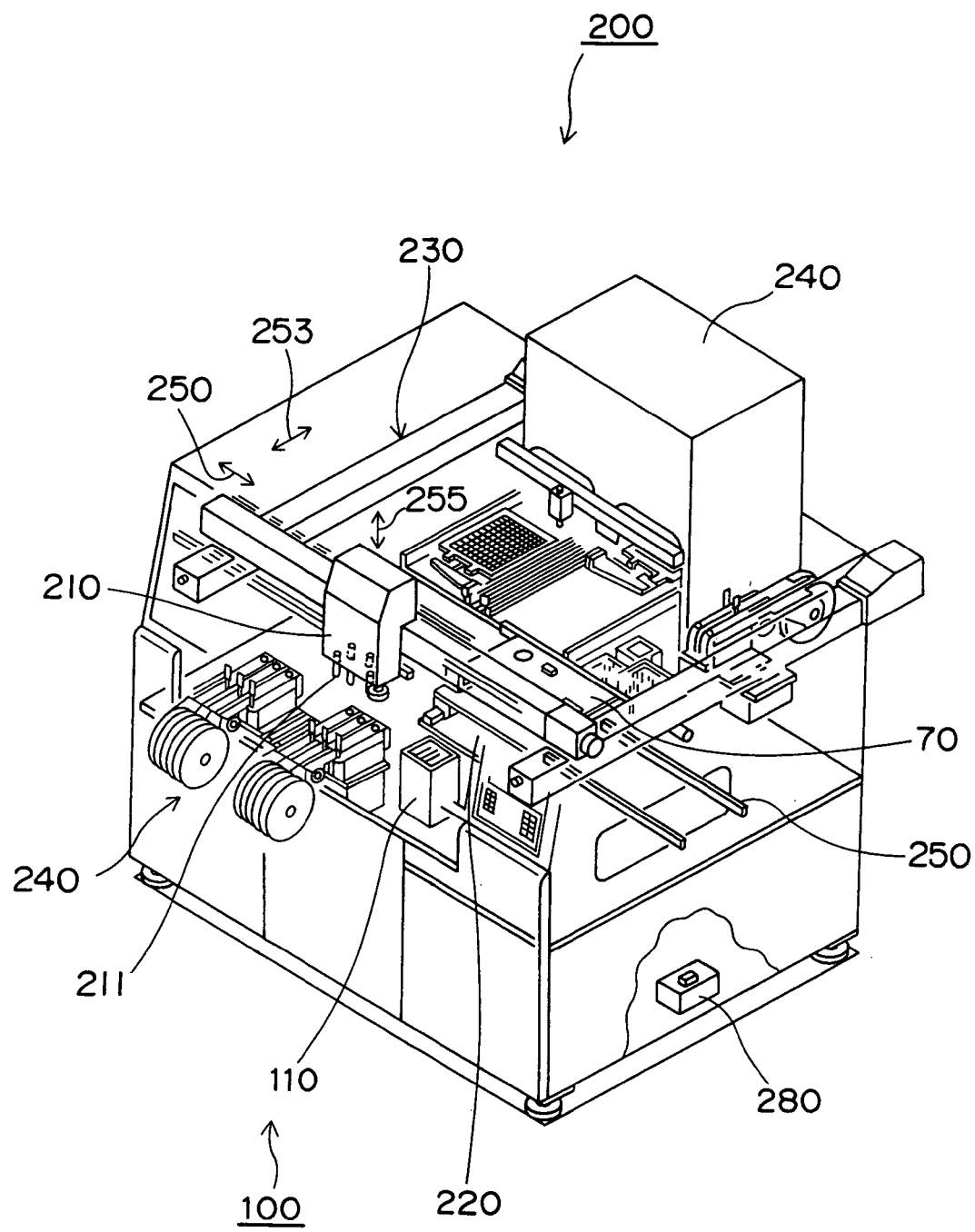
FIG. 8 is a perspective view of an electronic component mounting apparatus with the component image pickup apparatus of FIG. 1.

The component image pickup apparatus 100 constituted as above can be installed, for example, in an electronic component mounting apparatus 200 as shown in FIG. 8. In addition to the component image pickup apparatus 100, the electronic component mounting apparatus 200 has the component holding head 210, a drive unit 230 for moving the component holding head 210 in the movement direction 250 and the orthogonal direction 253, and a circuit board holding unit 220 for holding a circuit board 70 to which the electronic components 251 held by the suction nozzles 211 are to be mounted. In addition, the electronic component mounting apparatus 200 can include a component supply unit 240 for supplying electronic components 251, a transfer unit 250 for transferring the circuit board 70, and a controller 280 for the electronic component mounting apparatus 200.

Operations in the above-constructed component image pickup apparatus 100, that is, a component image pickup method will be depicted below by adopting an example of a component mounting operation carried out by the above component mounting apparatus 200. The description will be focused to only the image pickup operation supposed that components 251 are already held at suction nozzles 211. The image pickup operation is primarily controlled and carried out by the image pickup controller 115 as described earlier.

To the image pickup controller 150 is supplied a present position of the component holding head 210, i.e., present position information of each of suction nozzles 211-1 to 211-6 on the basis of a signal sent out by the drive unit 230. Meanwhile, a setting position of each of image pickup devices 111-1 to 111-3 is preliminarily detected. Therefore, the recognizer 150 can detect which of the suction nozzles 211 has been arranged above the image pickup device 111. Also the controller 280 has, for example, NC data or the like mounting related information necessary for mounting components supplied thereto. Conforming to a control by the controller 280, the component holding head 210 holds a determined component 251 by each of determined suction nozzles 211 in accordance with a mounting order. Since the mounting related information is also sent from the controller 280 to the recognizer 150, which of the components 251 is held by which of the suction nozzles 211, in other words, a relation between each suction nozzle 211 and the electronic component 251 held by the same is already detected at the recognizer 150 alike.

Because of being conformed to the mounting related information, components 251 are not always held by every suction nozzle 211. There are some cases in which one or a plurality of suction nozzles 211 do not hold components 251.

Figure 7:
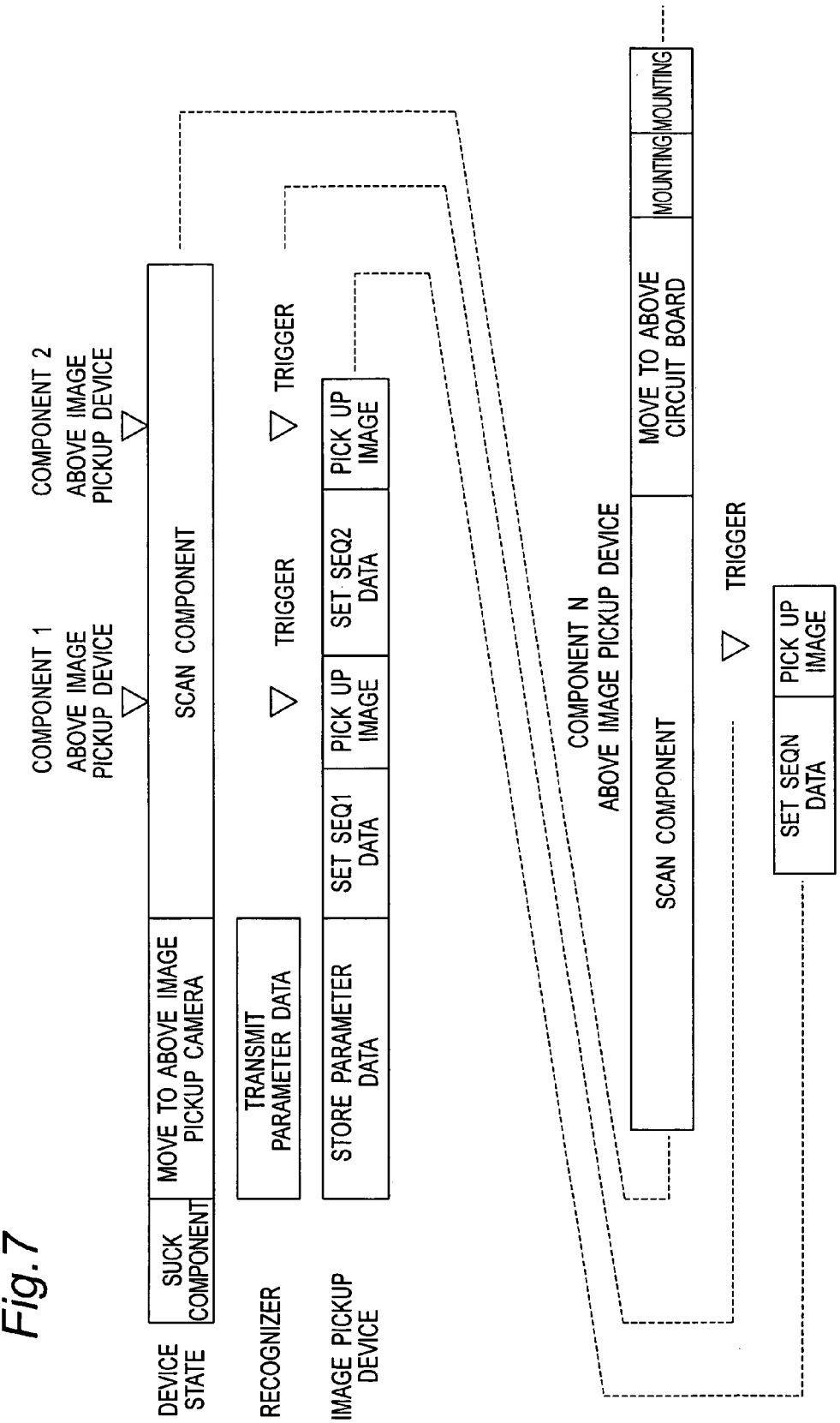
FIG. 7 is a diagram explanatory of the timing of the image pickup operation carried out by the component image pickup apparatus of FIG. 1.

As shown in FIG. 7, after suction nozzles 211 hold electronic components 251, the recognizer 150 sends the parameter data 160 corresponding to all electronic components 251 sucked in this time to the image pickup controller 115 of the image pickup camera 110 while the component holding head 210 moves to the image pickup camera 110. The storage 114 of the image pickup camera 110 stores the parameter data 160. The parameter data 160 includes also sequence data related to an order of imaging.

Figure 6:
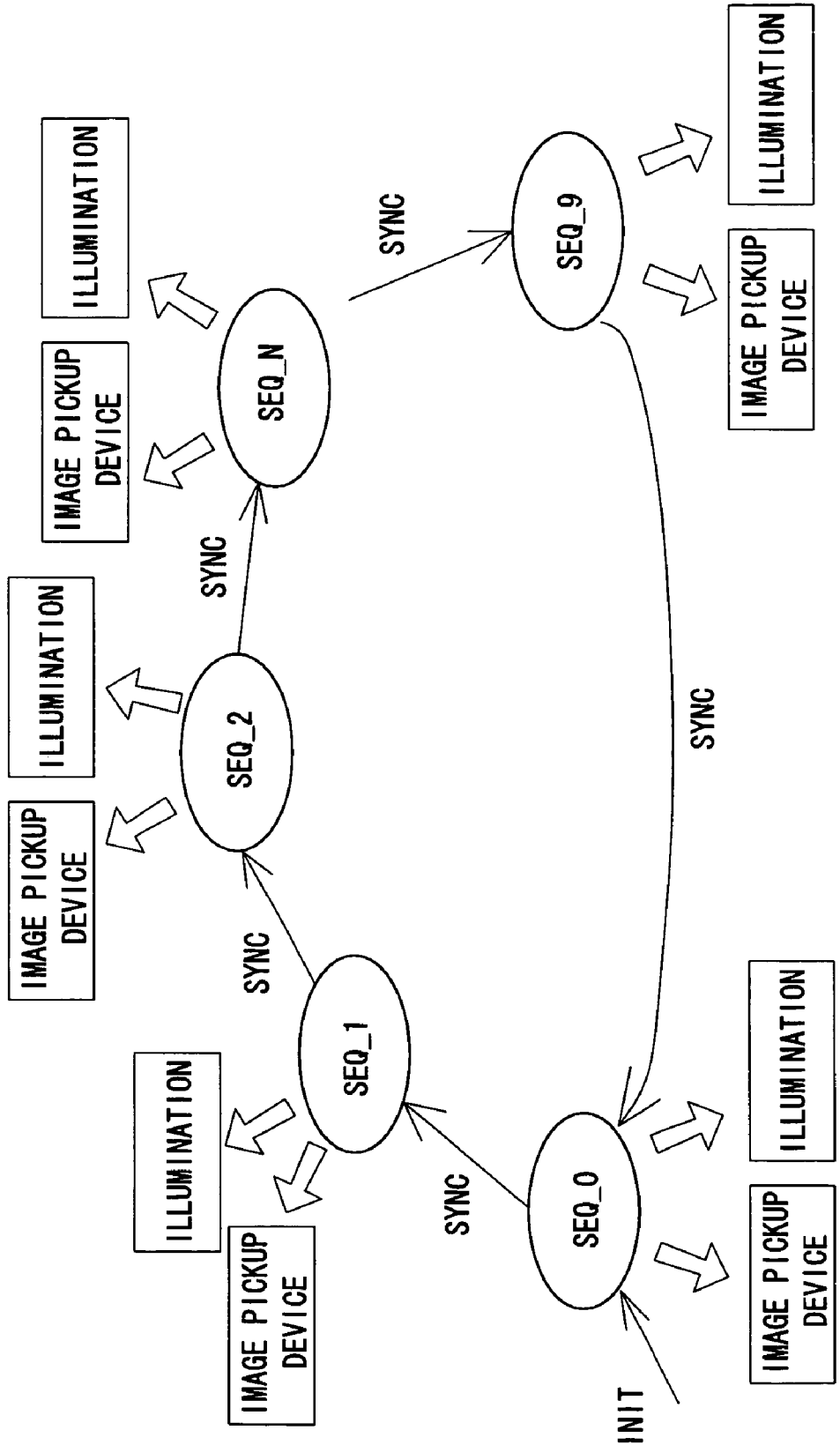
FIG. 6 is a state transition diagram explanatory of the image pickup operation carried out by the component image pickup apparatus of FIG. 1.

Referring further to FIG. 6, after the parameter data 160 is transferred to the image pickup camera 110 and before the first image pickup operation is started, the sequencer 113 reads out the image pickup condition and the illumination condition related to the first imaging (SEQ1) from the storage 114, sends the image pickup condition to the image pickup device 111 which is to carry out the first imaging, and sends the illumination condition to the illuminator 112. The image pickup device 111 for the first imaging switches an imaging visual field to large or small in accordance with the image pickup condition.

As described above, since the recognizer 150 has obtained the correspondence between the image pickup devices 111 and the suction nozzles 211 and has grasped the position information of each image pickup device 111, the sequencer 113 knows the imaging order. One that carries out the first imaging is the image pickup device 111-2 in the example as shown in FIG. 4A.

When the electronic component 251 sucked by the suction nozzle 211-2 enters the visual field of the image pickup device 111-2 as the component holding head 210 moves in the movement direction 250, the sequencer 113 instructs the image pickup device 111-2 and the illuminator 112 to pick up the image in accordance with the trigger signal generated by the recognizer 150. The illuminator 112 emits light by a luminance conforming to the illumination condition and the image pickup device 111-2 exposes the electronic component with the light.

After the image pickup is finished, the sequencer 113 reads out the image pickup condition and the illumination condition of a SEQ2 related to a second imaging from the storage 114, sends the image pickup condition to the image pickup device 111 which is to carry out the second imaging, i.e., the image pickup device 111-1 in the example as indicated in FIG. 4B and sends the illumination condition to the illuminator 112. The image pickup device 111-1 switches the visual field to large or small in accordance with the image pickup condition. When the electronic component 251 sucked by the suction nozzle 211-1 enters the visual field of the image pickup device 111-1, the sequencer 113 instructs the image pickup device 111-1 and the illuminator 112 to pick up the image according to the trigger signal generated by the recognizer 150. The illuminator 112 emits light by a luminance in conformity with the illumination condition and the image pickup device 111-1 exposes the electronic component with the light.

As is made clear with reference to FIGS. 3 and 4, through repetition of the above-described operation afterwards, the component 251 held by the suction nozzle 211-3, the component 251 held by the suction nozzle 211-6, the component 251 held by the suction nozzle 211-4, and the component 251 held by the suction nozzle 211-5 are imaged by the image pickup device 111-3 at the third imaging, by the image pickup device 111-1 at the fourth imaging, by the image pickup device 111-3 at the fifth imaging, and by the image pickup device 111-2 at the last imaging respectively and continuously, namely, while the component holding head 210 is moved at a constant velocity in the movement direction 250 without being stopped.

Each image pickup device 111 sends information on the image obtained at the time to the recognizer 150 after finishing the image pickup operation before starting the next image pickup operation.

According to the component image pickup apparatus 100 of the present embodiment, the plurality of image pickup devices 111 are adapted to pick up images one by one by shifting image pickup timing from each other, and moreover, the shift of the image pickup timing is made an amount for avoiding effects of the illumination light for the image pickup operation carried out immediately before. Because of the arrangement, all of the electronic components 251 can be imaged by one simple scan above the image pickup camera 110 in the movement direction 250. The hold posture of a plurality of components can be imaged separately without decreasing a cycle time.

The parameter data 160 having the image pickup condition and the illumination condition related to the sequence of the image pickup operation is preliminarily transferred to the image pickup camera 110 before the sequence of the image pickup operation is started. Therefore, the need of setting the image pickup condition and the illumination condition between the recognizer 150, and each image pickup device 111 and the illuminator 112 is eliminated when the image pickup operation is carried out by each image pickup device 111. A communication delay between the recognizer 150, and the image pickup devices 111 and the illuminator 112 is hence prevented, enabling moving the component holding head 210 at a higher velocity in the movement direction 250 as well as enabling the image pickup operation.

In the above embodiment, the image pickup devices 111 are operated to image one by one. This is to avoid the effect of the light for imaging onto the other image pickup operation in consequence of the short distance of electronic components 251 to be imaged as is discussed as the problem inherent in the conventional art. The technical concept of the present invention is to shift the image pickup timing to avoid the above effect for image pickup device present in a range where the light for imaging affects the other image pickup operation. Therefore, if components to be imaged are separated by a degree whereby the effect is avoided, it is possible to pick up the images concurrently at a plurality of image pickup devices. However, since the image pickup condition varies for every component as described before, it is impossible to unconditionally specify a range where the effect is avoided. The image pickup timing should be shifted at least in imaging adjacent components.

Although the electronic component is exemplified as the component to be imaged in the present embodiment, the component to be imaged is not limited to this.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A component image pickup apparatus including:
   a component holding head which has a plurality of component holding members and for moving in a movement direction; and
   an image pickup camera for picking up an image of each of components held by the component holding members,
   the image pickup camera comprising:
   a plurality of image pickup devices arranged corresponding to a plurality of paths respectively where the component holding members pass by the movement in the movement direction, for picking up the images of the components held by the component holding members;
   single illuminator arranged for the plurality of image pickup devices for applying light at an image pickup operation by each image pickup device; and
   an image pickup controller for controlling the image pickup operation to each image pickup device and the illuminator in accordance with an image pickup condition related to each image pickup device and set for every component and an illumination condition related to the illuminator.

2. The component image pickup apparatus according to claim 1, further comprising a recognizer connected to the image pickup camera for supplying the image pickup condition and the illumination condition to the image pickup controller before the component holding head reaches above the image pickup camera, controlling the image pickup operation to each image pickup device and the illuminator, and receiving image information from each image pickup device after the imaging.

3. The component image pickup apparatus according to claim 1, wherein the image pickup devices are disposed at respective setting positions where the image pickup devices pick up the images of components one by one with a time difference in accordance with the movement of the component holding members in the movement direction.

4. The component image pickup apparatus according to claim 2, wherein the image pickup devices are disposed at respective setting positions where the image pickup devices pick up the images of components one by one with a time difference in accordance with the movement of the component holding members in the movement direction.

5. The component image pickup apparatus according to claim 3, wherein the setting positions of a first image pickup device and a second image pickup device for imaging next to the first image pickup device are disposed at positions separated by at least a distance which is obtained by multiplying a moving velocity in the movement direction of the component holding head and an exposure time at the first image pickup device.

6. The component image pickup apparatus according to claim 4, wherein the setting positions of a first image pickup device and a second image pickup device for imaging next to the first image pickup device are disposed at positions separated by at least a distance which is obtained by multiplying a moving velocity in the movement direction of the component holding head and an exposure time at the first image pickup device.

7. The component image pickup apparatus according to claim 1, wherein the component holding members are arranged at equal intervals along a circumference, while the movement direction is a direction parallel to a diametrical direction of the circumference and passing through two of the component holding members arranged at the equal intervals.

8. The component image pickup apparatus according to claim 2, wherein the component holding members are arranged at equal intervals along a circumference, while the movement direction is a direction parallel to a diametrical direction of the circumference and passing through two of the component holding members arranged at the equal intervals.

9. The component image pickup apparatus according to claim 3, wherein the component holding members are arranged at equal intervals along a circumference, while the movement direction is a direction parallel to a diametrical direction of the circumference and passing through two of the component holding members arranged at the equal intervals.

10. The component image pickup apparatus according to claim 4, wherein the component holding members are arranged at equal intervals along a circumference, while the movement direction is a direction parallel to a diametrical direction of the circumference and passing through two of the component holding members arranged at the equal intervals.

11. The component image pickup apparatus according to claim 5, wherein the component holding members are arranged at equal intervals along a circumference, while the movement direction is a direction parallel to a diametrical direction of the circumference and passing through two of the component holding members arranged at the equal intervals.

12. The component image pickup apparatus according to claim 6, wherein the component holding members are arranged at equal intervals along a circumference, while the movement direction is a direction parallel to a diametrical direction of the circumference and passing through two of the component holding members arranged at the equal intervals.

13. A component image pickup method comprising:
supplying an image pickup condition and an illumination condition necessary for imaging each of components and set for every component to an image pickup camera while a component holding head with a plurality of component holding members moves to above the image pickup camera which has a plurality of image pickup devices for imaging respective components held by the component holding members, and single illuminator;
letting the component holding head pass above the image pickup camera along a movement direction without stopping the head after the supplying; and
sequentially imaging the components by the respective image pickup devices during the passing with a timing whereby effects of light for imaging of the illuminator are avoided.

14. A component mounting apparatus comprising:
a component image pickup apparatus;
a component holding head having a plurality of component holding members respectively for holding electronic components and mounting the held electronic components to a circuit board;
a drive unit for moving the component holding head in a movement direction; and
a circuit board holding unit for holding the circuit board,
the component image pickup apparatus including:
an image pickup camera for picking up an image of each of components held by the component holding members,
the image pickup camera having:
a plurality of image pickup devices arranged corresponding to a plurality of paths respectively where the component holding members pass by the movement in the movement direction, for picking up the images of the components held by the component holding members;
single illuminator arranged for the plurality of image pickup devices for applying light at an image pickup operation by each image pickup device; and
an image pickup controller for controlling the image pickup operation to each image pickup device and the illuminator in accordance with an image pickup condition related to each image pickup device and set for every component and an illumination condition related to the illuminator.

* * * * *